(12) United States Patent
Coteron Lopez et al.

(10) Patent No.: US 9,624,219 B2
(45) Date of Patent: Apr. 18, 2017

(54) COMPOUND (S) AND (R)-N-(2-FLUOROPYRIDIN-4-YL)-3-METHYL-2-(5-METHYL- 2,4-DIOXO-1,2-DIHYDROPYRIDO [3,4-D]PYRIMIDIN-3(4H)-YL)BUTANAMIDE AND USE

(71) Applicant: GlaxoSmithKline Intellectual Property Development Limited, Brentford, Middlesex (GB)

(72) Inventors: Jose-Miguel Coteron Lopez, Madrid (ES); Esther Pilar Fernandez Velando, Madrid (ES); Jorge Fernandez-Molina, Madrid (ES); Maria Luisa Leon-Diaz, Madrid (ES); David Matthew Wilson, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/132,274

(22) Filed: Apr. 19, 2016

(65) Prior Publication Data
US 2016/0311821 A1    Oct. 27, 2016

(30) Foreign Application Priority Data
Apr. 21, 2015   (EP) ...................... 15382200

(51) Int. Cl.
| C07D 471/04 | (2006.01) |
| A61K 31/519 | (2006.01) |
| A61K 45/06 | (2006.01) |

(52) U.S. Cl.
CPC .......... *C07D 471/04* (2013.01); *A61K 31/519* (2013.01); *A61K 45/06* (2013.01)

(58) Field of Classification Search
CPC ..... C07D 417/04; A61K 31/519; A61K 45/06
See application file for complete search history.

(56) References Cited

U.S. PATENT DOCUMENTS 8,431,608 B2 *  4/2013  Christos ............... C07D 471/04
                                                    514/393

FOREIGN PATENT DOCUMENTS

| WO | WO 2011/061277 A1 | 5/2011 |
| WO | WO 2015/189595 A1 | 12/2015 |
| WO | WO 2016/092326 A1 | 6/2016 |
| WO | WO 2016/162390 A1 | 10/2016 |

OTHER PUBLICATIONS

Lehane, et al. Molecular Microbiology, 94(2): 327-339 (Oct. 15, 2014).
Gamo, et al. Nature, 465(7296): 305-310 (May 20, 2010). Retrieved from the Internet: URL:http://www.nature.com/nature/journal/v465/n7296/full/nature09107.html.

* cited by examiner

*Primary Examiner* — Yong Chu
(74) *Attorney, Agent, or Firm* — Nicole Ho; Andrea V. Lockenour

(57) ABSTRACT

The present invention relates to a compound of Formula (I) having pharmacological activity, processes for its preparation, pharmaceutical compositions and their use in the treatment of certain parasitic certain parasitic protozoal infections such as malaria, in particular infection by *Plasmodium falciparum*.

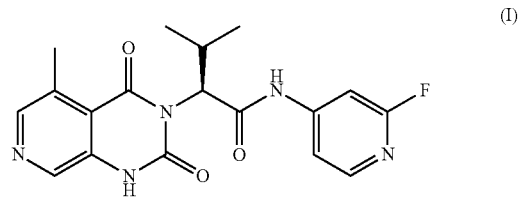

(S)—N-(2-fluoropyridin-4-yl)-3-methyl-2-(5-methyl-2,4-dioxo-1,2-dihydropyrido[3,4-d]pyrimidin-3(4H)-yl)butanamide.

9 Claims, No Drawings

COMPOUND (S) AND (R)-N-(2-FLUOROPYRIDIN-4-YL)-3-METHYL-2-(5-METHYL-2,4-DIOXO-1,2-DIHYDROPYRIDO[3,4-D]PYRIMIDIN-3(4H)-YL)BUTANAMIDE AND USE

FIELD OF THE INVENTION

The present invention relates to a novel dione compound having pharmacological activity, processes for its preparation, pharmaceutical compositions and their use in the treatment of certain parasitic protozoal infections such as malaria, in particular infection by *Plasmodium falciparum*.

BACKGROUND OF THE INVENTION

Parasitic protozoal infections are responsible for a wide variety of diseases of medical and veterinary importance, including malaria in man and various coccidioses in birds, fish and mammals. Many of the diseases are life-threatening to the host and cause considerable economic loss in animal husbandry, such as diseases caused by infection by species of *Eimeria, Theileria, Babesia, Cryptosporidium, Toxoplasma* (such as *Toxoplasma brucei*, African sleeping sickness and *Toxoplasma cruzi*, Chagas disease) and *Plasmodium* (such as *Plasmodium falciparum*), and the Mastigophora such as species of *Leishmania* (such as *Leishmania donovani*). Another parasitic organism of increasing concern is *Pneumocytis carinii*, which can cause an often fatal pneumonia in immunodeficient or immunocompromised hosts, including those infected with HIV.

Malaria is a mosquito-borne disease that, in humans, can be caused by five species of *Plasmodium* parasite, of which *Plasmodium falciparum* is the most virulent. In 2013, there were an estimated 128 million of people infected with malaria worldwide and malarial disease was responsible for an estimated 584,000 deaths (90% of them in sub-saharan Africa), young children and pregnant women being the most affected groups. In 2013, malaria killed an estimated 437,000 children under five years of age (WORLD HEALTH ORGANIZATION. (2014). *World malaria report*. Geneva, Switzerland, World Health Organization).

Resistance to classical treatments and emerging resistance to the current treatment of choice (artemisinins-based combination therapies) reveals the urgent need for new therapeutic agents with novel mechanisms of action (WORLD HEALTH ORGANIZATION. Joint assessment of the response to artemisinin resistance in the greater Mekong sub-region. November 2011-February 2012. Summary report.). In 2010, GSK released details of more than 13,500 chemical compounds that have already shown to inhibit *Plasmodium falciparum* parasite growth in the phenotypic screening approach (Gamo, F. J. et al. (2010) Thousands of chemical starting points for antimalarial lead identification. *Nature* 465, 305-310). Molecular structures and descriptions of these compounds were made publicly available in accessible databases under the name of TCAMS (Tres Cantos Antimalarial set) (http://www.ebi.ac.uk/chemblntd).

SUMMARY OF THE INVENTION

The present invention is directed to a novel dione compound for use in the treatment or chemotherapy of certain parasitic infections such as malaria, and in particular infection by *Plasmodium falciparum*, processes for its preparation and pharmaceutical compositions comprising such a compound.

DETAILED DESCRIPTION OF THE INVENTION

The present invention provides a compound of Formula (I):

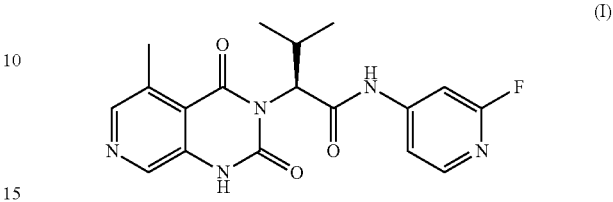

(I)

(S)—N-(2-fluoropyridin-4-yl)-3-methyl-2-(5-methyl-2,4-dioxo-1,2-dihydropyrido[3,4-d]pyrimidin-3(4H)-yl)butanamide or a pharmaceutically acceptable salt thereof.

Also included in the present invention are pharmaceutically acceptable salts. In certain embodiments of the invention, pharmaceutically acceptable salts of a compound of Formula (I) may be preferred over the respective free base because such salts impart greater stability or solubility to the molecule thereby facilitating formulation into a dosage form. Therefore, the present invention also covers the pharmaceutically acceptable salts of a compound of Formula (I). As used herein, the term "pharmaceutically acceptable salt" refers to a salt that retains the desired biological activity of the subject compound and exhibits minimal undesired toxicological effects. For a review on suitable salts see Berge et al, J. Pharm. Sci., 1977, 66, 1-19. The term "pharmaceutically acceptable salt" includes any pharmaceutically acceptable acid or basic addition salts. These pharmaceutically acceptable salts may be prepared in situ during the final isolation and purification of the compound, or by separately reacting the purified compound in its free base form with a suitable acid or base, respectively. The salt may precipitate from solution and be collected by filtration or may be recovered by evaporation of the solvent.

Therefore, according to a further aspect, the invention provides a pharmaceutically acceptable salt of a compound of Formula (I) thereof.

In another aspect, the invention provides a salt of a compound of Formula (I) thereof.

The compound of Formula (I) contains a basic functional group and is therefore capable of forming pharmaceutically acceptable acid addition salts by treatment with a suitable acid. A pharmaceutically acceptable acid addition salt may be formed by reaction of a compound of Formula (I) with a suitable strong inorganic or organic acid (such as hydrobromic, hydrochloric, sulfuric, nitric, phosphoric, perchloric, p-toluenesulfonic, benzenesulfonic, methanesulfonic, ethanesulfonic, 2-hydroxyethanesulfonic, naphthalenesulfonic (e.g. 2-naphthalenesulfonic), optionally in a suitable solvent such as an organic solvent, to give the salt which is usually isolated for example by crystallisation and filtration. Pharmaceutically acceptable acid addition salts include a hydrobromide, hydrochloride, hydroiodide, sulfate, bisulfate, nitrate, phosphate, perchlorate, p-toluenesulfonate, benzenesulfonate, methanesulfonate, ethanesulfonate, 2-hydroxyethanesulfonate, naphthalenesulfonate (e.g. 2-naphthalenesulfonate) or hemi-edisylate salt. In one embodiment, a pharmaceutically acceptable acid addition salt of a compound of Formula (I) is a salt of a strong acid, for example a hydrobromide, hydrochloride, hydroiodide, sulfate, nitrate, perchlorate, phosphate p-toluenesulfonic, benzenesulfonic or methanesulfonic salt.

Suitable pharmaceutically acceptable salts of a compound of Formula (I) include mono- or dibasic salts with the appropriate base. A pharmaceutically acceptable basic addition salt may be formed by reaction of a compound of Formula (I) with a suitable inorganic or organic base. Pharmaceutically acceptable basic addition salts include sodium, potassium, calcium, magnesium, ammonium, N-methylglucamine and choline salts The invention includes within its scope all possible stoichiometric and non-stoichiometric forms of the salts of a compound of Formula (I).

A compound of Formula (I) or a pharmaceutically acceptable salt thereof, may exist as solids or liquids, both of which are included in the invention. In the solid state, a compound of Formula (I) or a pharmaceutically acceptable salt thereof, may exist as either amorphous material or in crystalline form, or as a mixture thereof. It will be appreciated that a compound of Formula (I) or a pharmaceutically acceptable salt thereof, may exist in solvated or unsolvated form and may be formed wherein solvent molecules are incorporated into the crystalline lattice during crystallisation. Solvates may involve non-aqueous solvents such as ethanol, isopropanol, dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Therefore, in one aspect of the present invention, there is provided solvates of a compound of Formula (I), for example hydrates.

Salts of a compound of Formula (I) may be prepared by contacting appropriate stoichiometric amounts of the free base/acid with the appropriate acid/base in a suitable solvent. The free base/acid of a compound of Formula (I) may for example be in solution with the appropriate acid/base added as a solid or both the free base/acid of a compound of Formula (I) and the appropriate acid/base may independently be in solution.

Suitable solvents for solubilising a compound of Formula (I) free base include for example alcohols such as isopropanol; ketones such as acetone; acetonitrile or toluene. If the base is to be added as a solution in a solvent, the solvent used may include acetone, methanol or water.

The salts of a compound of Formula (I) may be isolated in solid form by conventional means from a solution thereof obtained as above. For example, a non-crystalline salt may be prepared by precipitation from solution, spray drying or freeze drying of solutions, evaporating a solution to a glass, or vacuum drying of oils, or solidification of melts obtained from reaction of the free base and the acid.

The salts of a compound of Formula (I) may be prepared by directly crystallising from a solvent in which the salt has limited solubility, or by triturating or otherwise crystallising a non-crystalline salt. For example, organic solvents such as acetone, acetonitrile, butanone, 1-butanol, ethanol, 1-propanol or tetrahydrofuran or mixtures of such solvents may be used. An improved yield of the salts may be obtained by the evaporation of some or all of the solvent or by crystallisation at elevated temperature followed by controlled cooling, for example in stages. Careful control of the precipitation temperature and seeding may be used to improve the reproducibility of the production process and the particle size distribution and form of the product.

Salts and solvates of a compound of Formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of a compound of Formula (I) or salts, solvates thereof and their pharmaceutically acceptable salts and solvates.

It will be appreciated by those skilled in the art that certain protected derivatives of a compound of Formula (I), which may be made prior to a final deprotection stage, may not possess pharmacological activity as such, but may, in certain instances, be administered orally or parenterally and thereafter metabolised in the body to form compounds defined in the first aspect which are pharmacologically active. Such derivatives may therefore be described as "prodrugs". Examples of suitable prodrugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compound of Formula (I). Suitable prodrugs for compounds of Formula (I) or salts or solvates thereof include: amides, carbamates, azo-compounds, phosphamides, glycosides.

As described above, a compound of Formula (I) may be in the form of its free base or a pharmaceutically acceptable salt, solvate, or prodrug of a compound of Formula (I), which upon administration to the recipient is capable of providing (directly or indirectly) a compound of Formula (I), or an active metabolite or residue thereof. Such pharmaceutically acceptable salts, solvates, and prodrugs are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives.

Furthermore, some of the crystalline forms of a compound of Formula (I) or salts (and solvates) thereof may exist in one or more polymorphic form, which are included in the present invention.

It will further be appreciated that a compound of Formula (I) may exist in different tautomeric forms. All possible tautomers are contemplated to be within the scope of the present invention.

A compound of Formula (I) or a pharmaceutically acceptable salt thereof can be useful in the treatment of certain parasitic infections such as parasitic protozoal infections by the malarial parasite *Plasmodium falciparum*, species of *Eimeria, Pneumocytis carinii, Trypanosoma cruzi, Trypanosoma brucei* or *Leishmania donovani*. In particular, a compound of Formula (I) or a pharmaceutically acceptable salt thereof can be useful for treatment of infection by *Plasmodium falciparum*. Accordingly, the invention is directed to methods of treating such infections. Therefore, there is provided a compound of Formula (I) or a pharmaceutically acceptable salt thereof, for use in therapy.

In one aspect of the invention there is provided a compound of Formula (I) or a pharmaceutically acceptable salt thereof for use in the treatment of a parasitic protozoal infection.

In another aspect of the invention there is provided a compound of Formula (I) or a pharmaceutically acceptable salt thereof for use in the treatment of malaria.

In another aspect of the invention, there is provided a compound of Formula (I) or a pharmaceutically acceptable salt thereof for use in the treatment of an infection by *Plasmodium falciparum*.

In another aspect of the invention, there is provided the use of a compound of Formula (I) or a pharmaceutically acceptable salt thereof in the manufacture of a medicament for the treatment of a parasitic protozoal infection.

In another aspect of the invention, there is provided the use of a compound of Formula (I) or a pharmaceutically acceptable salt thereof in the manufacture of a medicament for the treatment of malaria.

In another aspect of the invention, there is provided the use of a compound of Formula (I) or a pharmaceutically acceptable salt thereof in the manufacture of a medicament for the treatment of an infection by *Plasmodium falciparum*.

In a another aspect of the invention, there is provided a method for the treatment of a human or animal subject suffering from a parasitic protozoal infection, which method comprises administering to said human or animal subject an effective amount of a compound of Formula (I) or a pharmaceutically acceptable salt thereof.

In another aspect of the invention, there is provided a method for the treatment of a human or animal subject suffering from malaria, which method comprises administering to said human or animal subject an effective amount of a compound of Formula (I) or a pharmaceutically acceptable salt thereof.

In another aspect of the invention, there is provided a method for the treatment of a human or animal subject suffering from a parasitic protozoal infection by *Plasmodium falciparum*, which method comprises administering to said human or animal subject an effective amount of a compound of Formula (I) or a pharmaceutically acceptable salt thereof.

The methods of treatment of the invention comprise administering a safe and effective amount of a compound according to Formula (I), and a pharmaceutically acceptable salt thereof to a patient in need thereof.

As used herein, "treatment" means: (1) the amelioration or prevention of the condition being treated or one or more of the biological manifestations of the condition being treated, (2) the interference with (a) one or more points in the biological cascade that leads to or is responsible for the condition being treated or (b) one or more of the biological manifestations of the condition being treated, or (3) the alleviation of one or more of the symptoms or effects associated with the condition being treated. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "effective amount" or "safe and effective amount" means an amount of the compound sufficient to significantly induce a positive modification in the condition to be treated but low enough to avoid serious side effects (at a reasonable benefit/risk ratio) within the scope of sound medical judgment. A safe and effective amount of a compound of Formula (I) or a pharmaceutically acceptable salt thereof will vary with the route of administration chosen; the nature of the infection and/or condition being treated; the severity of the infection and/or condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal subject.

A compound of Formula (I) or a pharmaceutically acceptable salt thereof may be administered by any suitable route of administration, including systemic administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages.

A compound of Formula (I) or a pharmaceutically acceptable salt thereof may be administered once only, or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. The dosage will also vary according to the nature of the intended treatment, wherein "treatment" is as herein defined, for example a greater dose of compound may be given for amelioration as compared with prevention of a condition being treated. Suitable dosing regimens for a compound of the invention depend on the pharmacokinetic properties of that compound, such as absorption, distribution, and half-life, which can be determined by the skilled artisan. In addition, suitable dosing regimens including the duration such regimens are administered, depend on the route of administration of the compound, on the condition being treated, the severity of the condition being treated, the age and physical condition of the patient being treated, the medical history of the patient to be treated, the nature of any concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. It will also be appreciated that if a compound of Formula (I) or a pharmaceutically acceptable salt thereof is administered in combination with one or more additional active therapeutic agents as discussed further hereinbelow, the dosing regimen of the compound of the invention may also vary according to the nature and amount of the one or more additional active therapeutic agents as necessary.

Typical dosages of a compound of Formula (I) may vary depending upon the particular route of administration chosen. Typical dosages for oral administration are predicted to be in a range from about 35 to about 1000 mg/kg. Typically a compound of Formula (I) may be administered once a day, once every two days or even up to once weekly.

In another aspect of the invention, a pharmaceutical composition comprising a compound of Formula (I) or a pharmaceutically acceptable salt thereof may be adapted for oral administration.

A compound of Formula (I) or a pharmaceutically acceptable salt thereof may also be used in combination with other active therapeutic agents. The invention thus provides, in a further aspect, a combination comprising a compound of Formula (I) or a pharmaceutically acceptable salt thereof together with a further active therapeutic agent. When a compound of Formula (I) or a pharmaceutically acceptable salt thereof is used in combination with a second active therapeutic agent which is active against the same disease state the dose of each compound may differ from that when each compound is used alone. Appropriate doses will be readily appreciated by those skilled in the art. It will be appreciated that the amount of a compound of Formula (I) or pharmaceutically acceptable salts required for use in treatment will vary with the nature of the condition being treated and the age and the condition of the patient and will be ultimately at the discretion of the attendant physician or veterinarian.

A compound of Formula (I) or a pharmaceutically acceptable salt thereof may be used alone or in combination with one or more additional active therapeutic agents, such as other antiparasitic drugs, for example antimalarial drugs.

Such other active therapeutic agents include antimalarial drugs such as (e.g. chloroquine, mefloquine, primaquine, pyrimethamine, quinine, artemisinin, halofantrine, doxycycline, amodiaquine, atovaquone, tafenoquinedapsone, proguanil, sulfadoxine, cycloguanil) and fansidar.

The combinations referred to above may conveniently be presented for use in the form of a pharmaceutical formulation and thus pharmaceutical formulations comprising a combination as defined above together with a pharmaceutically acceptable carrier and/or excipient comprise a further aspect of the invention. The individual components of such combinations may be administered either sequentially or simultaneously in separate or combined pharmaceutical formulations by any convenient route.

When administration is sequential, either a compound of Formula (I) or a pharmaceutically acceptable salt thereof, or the one or more additional active therapeutic agent(s) may be administered first. When administration is simultaneous, the combination may be administered either in the same or different pharmaceutical composition. When combined in the same formulation it will be appreciated that a compound of Formula (I) or a pharmaceutically acceptable salt thereof, and the one or more additional active therapeutic agent(s) must be stable and compatible with each other and the other components of the formulation. When formulated separately a compound of Formula (I) or a pharmaceutically acceptable salt thereof, and the one or more additional active therapeutic agent(s) may be provided in any convenient formulation, conveniently in such manner as are known for such compounds in the art.

Compositions

A compound of Formula (I) or a pharmaceutically acceptable salt thereof will normally, but not necessarily, be formulated into pharmaceutical compositions prior to administration to a patient. In one aspect, the invention is directed to pharmaceutical compositions comprising a compound of Formula (I) or a pharmaceutically acceptable salt thereof. In another aspect the invention is directed to a pharmaceutical composition comprising (a) a compound of Formula (I) or a pharmaceutically acceptable salt thereof and (b) one or more pharmaceutically acceptable carriers and/or excipients. In another aspect, the invention provides a pharmaceutical composition comprising a compound of Formula (I) or a pharmaceutically acceptable salt thereof. In a further aspect, the invention provides a pharmaceutical composition comprising (a) a compound of Formula (I) or a pharmaceutically acceptable salt thereof and (b) one or more pharmaceutically acceptable carriers. In a further aspect, the invention provides a pharmaceutical composition comprising (a) a compound of Formula (I) or a pharmaceutically acceptable salt thereof and (b) a pharmaceutically acceptable carrier.

The carrier and/or excipient must be "acceptable" in the sense of being compatible with the other ingredients of the formulation and not deleterious to the recipient thereof.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from about 0.1 to 1000 mg, in another aspect 0.1 mg to about 500 mg of a compound of the invention.

The pharmaceutical compositions of the invention typically contain a compound of Formula (I) or a pharmaceutically acceptable salt thereof. In addition, the pharmaceutical compositions of the invention may optionally further comprise one or more additional active therapeutic compounds. The pharmaceutical compositions of the invention typically contain more than one pharmaceutically acceptable excipient. However, in certain embodiments, the pharmaceutical compositions of the invention contain one pharmaceutically acceptable excipient.

A compound of Formula (I) or a pharmaceutically acceptable salt thereof, and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; and (5) inhalation such as aerosols and solutions.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carriage or transport of a compound of Formula (I) or a pharmaceutically acceptable salt thereof from one organ, or portion of the body, to another organ, or portion of the body, once administered to the patient. Certain pharmaceutically acceptable excipients may be chosen for their ability to enhance patient compliance.

Suitable pharmaceutically acceptable excipients include the following types of excipients: binders, disintegrants, lubricants, glidants, granulating agents, coating agents, wetting agents, solvents, co-solvents, suspending agents, emulsifiers, sweeteners, flavouring agents, flavour masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

In one aspect, the invention is directed to a solid or liquid oral dosage form such as a liquid, tablet, lozenge or a capsule, comprising a safe and effective amount of a compound of the invention and a carrier. The carrier may be in the form of a diluent or filler. Suitable diluents and fillers in general include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. A liquid dosage form will generally consist of a suspension or solution of the compound or pharmaceutically acceptable salt in a liquid carrier for example, ethanol, olive oil, glycerine, glucose (syrup) or water (e.g. with an added flavouring, suspending, or colouring agent). Where the composition is in the form of a tablet or lozenge, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers or a semi solid e.g. mono di-glycerides of capric acid, Gelucire™ and Labrasol™, or a hard capsule shell e.g. gelatin. Where the composition is in the form of a soft shell capsule e.g. gelatin, any pharmaceutical carrier routinely used for preparing dispersions or suspensions may be considered, for example aqueous gums or oils, and may be incorporated in a soft capsule shell.

An oral solid dosage form may further comprise an excipient in the form of a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise an excipient in the form of a disintegrant. Suitable disintegrants include crospovidone, sodium starch glycolate, croscarmelose, alginic acid, and sodium carboxymethyl cellulose. The oral solid dosage form may further comprise an excipient in the form of a lubricant. Suitable lubricants include stearic acid, magnesium stearate, calcium stearate, and talc.

There is further provided by the present invention a process of preparing a pharmaceutical composition, which process comprises mixing the compound of Formula (I) or a pharmaceutically acceptable salt thereof, together with a pharmaceutically acceptable carrier and/or excipient.

Preparations for oral administration may be suitably formulated to give controlled/extended release of the active compound.

Processes

A general procedure for acid chloride formation and amide formation is described in the literature (*J. Chem. Res.* 2008 (22), 530-533) using appropriate commercially available acids and anilines as starting materials.

The compound of formula (I) may be synthesised by asymmetric or non-asymmetric routes. One such asymmetric route is shown in the following Scheme.

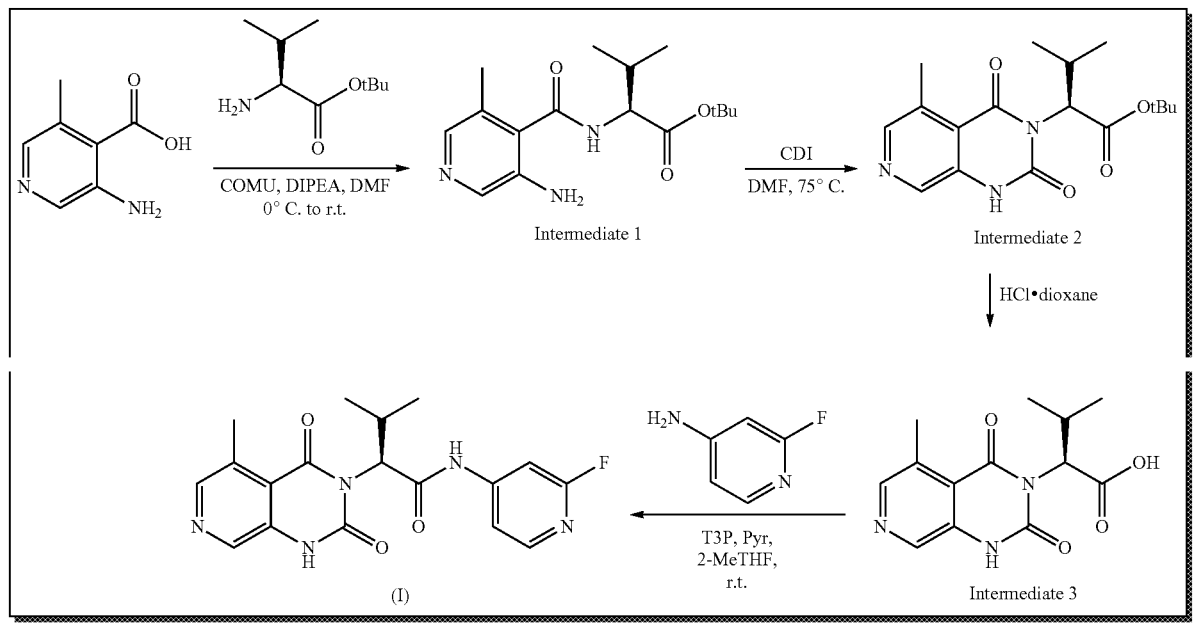

Preparation of a compound of formula (I) by non-asymmetric means and subsequent purification may result in the (R) enantiomer of the compound of formula (I) or a salt thereof being present as an impurity (ie (R)—N-(2-fluoropyridin-4-yl)-3-methyl-2-(5-methyl-2,4-dioxo-1,2-dihydropyrido[3,4-d]pyrimidin-3(4H)-yl)butanamide).

It will be readily apparent to those skilled in the art that the compound of Formula (I) may be prepared using methods analogous to those outlined above, or by reference to the experimental procedures detailed in the Examples provided herein. Further details for the preparation of the compound of Formula (I) are found in the Examples.

With appropriate manipulation and protection of any chemical functionality, the synthesis of a compound of Formula (I) is accomplished by methods analogous to those above. In any particular case, particular protecting groups may be required. Suitable protecting groups can be found, but are not restricted to, those found in T W Greene and P G M Wuts 'Protective Groups in Organic Synthesis', 3$^{rd}$ Ed (1999), J Wiley and Sons.

EXPERIMENTAL

Abbreviations

In describing the invention, chemical elements are identified in accordance with the Periodic Table of the Elements. Abbreviations and symbols utilised herein are in accordance with the common usage of such abbreviations and symbols by those skilled in the chemical arts. The following abbreviations are used herein:
Anh anhydrous
Aq. Aqueous
AWCI Antimalarial whole cell Screening
cat. Catalytic
CDI Carbonyldiimidazole
COMU 1-Cyano-2-ethoxy-2-oxoethylidenaminooxy)dimethylamino-morpholino-carbenium hexafluorophosphate
conc. concentrated
DCM Dicloromethane
DIPEA Diisopropylethylamine
DMF Dimethylformamide
DMSO-d6 Deuterated dimethylsulfoxide
EtOAc Ethyl acetate
ES MS Electrospray mass spectrometry
g grams
h Hours
HPLC High performance liquid chromatography
HTS High throughput screening
iPrOH 2-Propanol
iPr2O Diisopropyl ether
M Molar
MeOH Methanol
min(s) Minutes
mL milliliters
mmol millimoles
mg milligrams
MW Microwave
N Normal
$^1$H NMR proton nuclear magnetic resonance spectroscopy
quant. quantitative
rt room temperature
sat. saturated
THF tetrahydrofuran
T3P Propylphosphonic anhydride
° C. degrees centigrade Compound Preparation Examples The following Examples illustrate the invention. These Examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

Where materials were commercially available, this is indicated in parentheses after the compound name, in capitals. For example, in the preparation of Intermediate 3-amino-5-methylisonicotinic acid, hydrochloride was purchased from ANICHEM, so it is stated "3-amino-5-methylisonicotinic acid, hydrochloride (ANICHEM)".

Intermediate 1 (S)-tert-butyl 2-(3-amino-5-methylisonicotinamido)-3-methylbutanoate

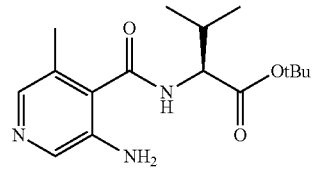 [SMILES: Cc1cncc(N)c1C(=O)N[C@H](C(=O)OC(C)(C)C)C(C)C]

To a solution of 3-amino-5-methylisonicotinic acid, hydrochloride (ANICHEM, 500 mg, 2.65 mmol) and (S)-tert-butyl 2-amino-3-methylbutanoate, hydrochloride (612 mg, 2.92 mmol) in 10 mL of anhydrous DMF under N$_2$ atmosphere at 0° C., DIPEA (1.852 mL, 10.60 mmol) and COMU (ALDRICH, 1249 mg, 2.92 mmol) were added. The resulting mixture was stirred at 0° C. for 1 h and then at room temperature for 2 hours. The reaction was poured into iced brine (100 mL) and then it was extracted with EtOAc (3×75 mL). The combination of the organic layers was washed with 10% NaHCO$_3$ and brine, dried over MgSO$_4$, filtered and concentrated under reduced pressure. The resulting crude was purified by flash chromatography (Isolute, NH$_2$—SiO$_2$, CyHex-EtOAc gradients from 100:0 to 35:65 to 10:90) to give 470 mg of (S)-tert-butyl 2-(3-amino-5-methylisonicotinamido)-3-methylbutanoate (470 mg, 1.529 mmol, 57.7%) as a brown oil.

$^1$H NMR (400 MHz, CDCl3) δppm: 7.93 (s, 1H), 7.80 (s, 1H), 6.51 (d, 1H), 4.61 (dd, 1H), 4.40 (br. S, 2H), 2.31 (m, 1H), 2.30 (s, 3H), 1.50 (s, 9H), 1.05 (d, 3H), 0.97 (d, 3H). [ES+MS] m/z 308 (M+H).

Intermediate 2 (S)-tert-butyl 3-methyl-2-(5-methyl-2,4-dioxo-1,2-dihydropyrido[3,4-d]pyrimidin-3(4H)-yl)butanoate

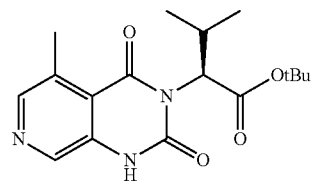 [SMILES: Cc1cncc2[nH]c(=O)n([C@H](C(=O)OC(C)(C)C)C(C)C)c(=O)c12]

To a solution of (S)-tert-butyl 2-(3-amino-5-methylisonicotinamido)-3-methylbutanoate (for example as prepared in Intermediate 1, 470 mg, 1.529 mmol) in 10 mL of toluene under N$_2$ atmosphere, CDI (ALDRICH, 545 mg, 3.36 mmol) was added and the resulting solution was heated at 50° C. for 1 h and the mixture was heated at 90° C. for 3.5 h. The reaction was treated with water (20 mL) and EtOAc (25 mL) and the layers were separated. The aqueous layer was extracted with EtOAc (25 mL). The combination of the organic layers was washed with brine (20 mL), dried over anhydrous MgSO₄, filtered and concentrated under reduced pressure. The resulting crude was purified by flash chromatography (20 g Merck, CyHex:EtOAc gradients from 80:20 to 50:50 to 10:90) to give 0.44 g of (S)-tert-butyl 3-methyl-2-(5-methyl-2,4-dioxo-1,2-dihydropyrido[3,4-d]pyrimidin-3(4H)-yl)butanoate (440 mg, 1.320 mmol, 86% yield) as a white solid.

$^1$H NMR (400 MHz, DMSO-d6) δppm: 11.82 (br. s, 1H), 8.46 (s, 1H), 8.25 (d, 1H), 4.89 (d, 1H), 2.62 (s, 3H), 2.59 (m, 1H), 1.32 (s, 9H), 1.15 (d, 3H), 0.70 (d, 3H). [ES+MS] m/z 334 (M+H).

Intermediate 3 (S)-3-methyl-2-(5-methyl-2,4-dioxo-1,2-dihydropyrido[3,4-d]pyrimidin-3(4H)-yl)butanoic acid, hydrochloride

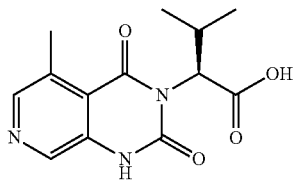 [SMILES: Cc1cncc2[nH]c(=O)n([C@H](C(=O)O)C(C)C)c(=O)c12]

To (S)-tert-butyl 3-methyl-2-(5-methyl-2,4-dioxo-1,2-dihydropyrido[3,4-d]pyrimidin-3(4H)-yl)butanoate (for example as prepared in Intermediate 2, 3.962 g, 11.88 mmol), hydrogen chloride solution 4M in 1,4-dioxane (ALDRICH, 80 mL, 320 mmol) was added at 0° C. and the reaction mixture was kept at rt for 8 h. The reaction mixture was concentrate under reduced pressure to give a solid that was triturated with iPr₂O (20 mL) and then with EtOAc (15 mL) and the solid obtained was filtrated. The resulting solid was recovered with MeOH and the solvent evaporate to give a thick oil, triturated with iPr₂O (20 mL) to give (S)-3-methyl-2-(5-methyl-2,4-dioxo-1,2-dihydropyrido[3,4-d]pyrimidin-3(4H)-yl)butanoic acid hydrochloride (3086 mg, 11.13 mmol, 93% yield).

$^1$H NMR (400 MHz, DMSO-d6) δppm: 11.92 (s, 1H), 8.74 (br. s, 1H), 8.52 (s, 1H), 8.28 (d, 1H), 4.94 (d, 1H), 2.63 (s, 3H), 2.60 (m, 1H), 1.17 (d, 3H), 0.70 (d, 3H). [ES+MS] m/z 278 (M+H).

Example 1

(S)—N-(2-fluoropyridin-4-yl)-3-methyl-2-(5-methyl-2,4-dioxo-1,2-dihydropyrido[3,4-d]pyrimidin-3(4H)-yl)butanamide

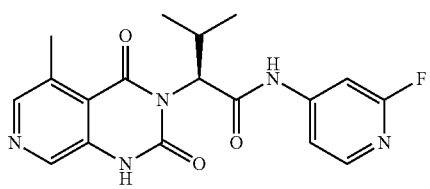 [SMILES: Cc1cncc2[nH]c(=O)n([C@H](C(=O)Nc3ccnc(F)c3)C(C)C)c(=O)c12]

T3P (ALDRICH, 50 wt % solution in EtOAc, 857 uL, 1.44 mmol) was added to a stirred solution of 2-fluoropyridin-4-amine (ALDRICH, 64 mg, 0.57 mmol), pyridine (ALDRICH, 175 uL, 2.16 mmol) and (2S)-3-methyl-2-{5-methyl-2,4-dioxo-1H,2H,3H,4H-pyrido[3,4-d]pyrimidin-3-yl}butanoic acid hydrochloride (for example as prepared in Intermediate 3, 150 mg, 0.48 mmol) in EtOAc (2 mL) and DMF (1 mL) at 0° C. The reaction mixture was stirred at 0° C. for 6 hours. The reaction mixture was allowed to stand in the refrigerator at 4° C. overnight and then it was allowed to warm to room temperature for 10 hours. Then, the reaction was left overnight at room temperature. The reaction mixture was cooled to 0° C. and poured into ice cold sodium bicarbonate solution (50 mL) and extracted with EtOAc (100+50 mL). The combined organic phases were washed with half-saturated sodium bicarbonate solution (50 mL) and brine (50 mL), dried over sodium sulphate, diluted with toluene (25 mL) and evaporated under reduced pressure. The residue was co-evaporated twice with toluene (25 mL) then purified by chromatography on silica gel (SNAP 25, eluting with a gradient of 0.5-5% MeOH in DCM) to give (S)—N-(2-fluoropyridin-4-yl)-3-methyl-2-(5-methyl-2,4-dioxo-1,2-dihydropyrido[3,4-d]pyrimidin-3(4H)-yl)butanamide (181 mg) as a white solid.

1H NMR (400 MHz, DMSO-d6) δppm: 11.78 (s, 1H), 10.09 (s, 1H), 8.45 (s, 1H), 8.28 (s, 1H), 8.08 (d, 1H), 7.41 (m, 1H), 7.39 (s, 1H), 5.77 (s, 1H), 5.08 (d, 1H), 2.70 (m, 1H), 2.63 (s, 3H), 1.17 (d, 3H), 0.73 (d, 3H). [ES+MS] m/z 372 (M+H). 93.8% ee (Chiralpak AD-H (25×0.46 cm), 5 μm, n-Hexane/Ethanol 80/20% v/v, flow 0.8 mL/min, 3.1% a/a by UV (9.9 min) and 96.9% a/a by UV (15.1 min)).

Biological Assays

A compound of this invention may be tested in one of several biological assays to determine the concentration of compound which is required to have a given pharmacological effect. The assays are described below.

In Vitro Potency

P. falciparum Growth Inhibition Assay.

The sensitivity of P. falciparum infected erythrocytes to the compound is determined in triplicate using the [$^3$H] hypoxanthine incorporation method with an inoculum of 0.5% parasitemia (ring stage) and 2% hematocrit. The parasites were grown in RPMI 1640 and supplemented with 5% Albumax (or 10% serum). Plates are incubated at 37° C., 5% CO₂, 5% O₂, 90% N₂. After 24 h of incubation, [$^3$H]hypoxanthine is added and plates are incubated for another 24 h. After that period, plates are harvested on a glass fiber filter using a TOMTEC Cell harvester 96. Filters are dried and melt on scintillator sheets and the bound radioactivity is quantified by use of a Wallac Microbeta Trilux (Model 1450 LS-Perkin Elmer). IC₅₀s are determined using Grafit 5 program (Grafit program; Erithacus Software, Horley, Surrey, United Kingdom).

Results

The average Pf IC₅₀ on P. Falciparum Pf3D7A for Example 1 was 0.032.

In Vivo Efficacy

P. falciparum In Vivo Efficacy Assay.

Antimalarial in vivo efficacy was determined using the P. falciparum mouse model following the procedure described in: Jimenez-Diaz, M. B., Mulet, T., Viera, S., Gómez, V., Garuti, H., Ibañez, J., Alvarez-Doval, A., Shlutz, D. L., Martinez, A., Improved Murine Model Of Malaria Using Plasmodium falciparum (Competent Strains and Non-Myelodepleted NOD-scid IL2R_null Mice Engrafted with Human Erythrocytes) Antimicrob. Agents Chemother 2009, 53 (10), 4533-4536.

The goal of this study is to assess the therapeutic efficacy of Example 1 against Plasmodium falciparum Pf3D7$^{0087/N9}$ growing in peripheral blood of NODscidIL2Rγ$^{null}$ mice engrafted with human erythrocytes. The levels of Example 1 are measured in serial peripheral blood samples obtained from each mouse of the efficacy experiment during the first 23 hrs after the first dose. The area under the curve of levels of compound is used to estimate the exposure in blood during the first 23 hours after the first administration (AUC0-23h).

The effect of Example 1 on *P. Falciparum* Pf3D7$^{0087/N9}$ was assessed by microscopy and flow cytometry.

Results

The mean $ED_{90}$ (mg/kg)/$AUC_{ED90}$ (μg·h·mL-1·day-1) for Example 1 was 0.53/0.18 (interval of confidence 95%).

Solubility Assessment in FaSSIF

Solvents and Buffers

Organic solvents of HPLC grade were used. Ultra pure water (Milli-Q grade) was used. Buffers were prepared with ultra pure water and filtered using 0.45μ nylon filters.

I. Procedure.

Determination of Equilibrium Solubility (Assuming Chemical Stability in the Desired Solvent is not a Problem).

a) 1 mg of solid compound was weighted in one 4 mL glass vial and 1 mL of FaSSIF was added. All these samples were prepared by duplicate.
b) The samples were stirred (roller mixer) for 4 hr at room temperature. If required, additional solid compound (0.1 mg) was added to maintain excess of it (saturated solutions).
c) After 4 hours, the samples were centrifuged (10000 rpm, 10 min.) and the supernatants were transfer to an HPLC vial and analysed by LC-MS (previous dilution with mobile phase when needed).
d) The pH of the final solution in each sample was measured with a pH-meter (WTW pH330i and a pH-electrode Sentix 41).

LC-MS Assay for Analytical Quantification

All supernatants were analysed by LC-MS. Quantification of those samples was carried out against calibration curves obtained from 1 mg/mL DMSO (Aldrich cat. ref.: 27685-5) stock solutions, by dilution with the mobile phase used in the chromatography. Depending on the solubility range, U.V. (1 μg/mL to 100 μg/mL) or MS (1 μg/mL to 1 ng/mL) detector were used in the quantification.

Analysis of Data

The analysis of all LC-MS data was performed with MassLynx 3.4 software and Analyst 1.4.2. Statistical and graphic analysis of data was performed using Microsoft Excel. The concentration (μM) and solubility (μg/mL) for each compound was calculated using the peak areas from the sample and those from the calibration curve.

Results

The solubility of Example 1 in FaSSIF was 426 (μg/mL)

All publications, including but not limited to patents and patent applications cited in this specification are herein incorporated by reference as if each individual publication were specifically and individually indicated to be incorporated by reference as though fully set forth.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The invention claimed is:

1. A compound of Formula (I)

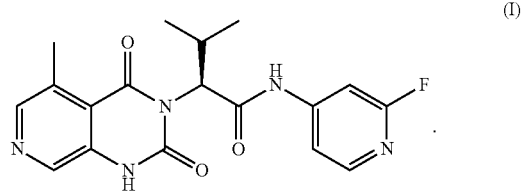 [SMILES: Cc1cncc2[nH]c(=O)n([C@H](C(=O)Nc3ccnc(F)c3)C(C)C)c(=O)c12]

2. A pharmaceutically acceptable salt of a compound of Formula (I) as defined in claim 1.

3. A pharmaceutical composition comprising (a) a compound of Formula (I) as defined in claim 1 and (b) one or more pharmaceutically acceptable carriers.

4. A combination comprising (a) a compound Formula (I) as defined in claim 1 and (b) at least one anti-malarial agent.

5. A method for the treatment of a human or animal subject suffering from a parasitic protozoal infection, comprising administering to said human or animal subject an effective amount of a compound of Formula (I) as defined in claim 1.

6. A mixture comprising a compound of Formula (I) as defined in claim 1 and (R)—N-(2-fluoropyridin-4-yl)-3-methyl-2-(5-methyl-2,4-dioxo-1,2-dihydropyrido[3,4-d]pyrimidin-3(4H)-yl)butanamide.

7. A method for the treatment of a human subject suffering from a parasitic protozoal infection, comprising administering to said human subject an effective amount of a compound of Formula (I) as defined in claim 1.

8. The method of claim 7, wherein the parasitic protozoal infection is malaria.

9. The method of claim 7, wherein the parasitic protozoal infection is *Plasmodium falciparum*.

* * * * *